United States Patent
Herrmann et al.

(10) Patent No.: US 9,535,011 B2
(45) Date of Patent: Jan. 3, 2017

(54) EMPTY BOTTLE INSPECTION

(75) Inventors: Marius Michael Herrmann, Rosenheim (DE); Heinrich Wiemer, Hamburg (DE); Wolfgang Schorn, Hönningen (DE); Jürgen Herrmann, Rosenheim (DE)

(73) Assignee: KHS GmbH, Dortmund (DE)

( * ) Notice: Subject to any disclaimer, the term of this patent is extended or adjusted under 35 U.S.C. 154(b) by 432 days.

(21) Appl. No.: 14/125,180

(22) PCT Filed: May 2, 2012

(86) PCT No.: PCT/EP2012/001895
§ 371 (c)(1),
(2), (4) Date: Mar. 24, 2014

(87) PCT Pub. No.: WO2012/167860
PCT Pub. Date: Dec. 13, 2012

(65) Prior Publication Data
US 2014/0226005 A1    Aug. 14, 2014

(30) Foreign Application Priority Data
Jun. 10, 2011   (DE) .................. 10 2011 106 136

(51) Int. Cl.
| | | |
|---|---|---|
| H04N 7/18 | (2006.01) | |
| G01N 21/90 | (2006.01) | |
| G01N 21/27 | (2006.01) | |
| G06T 7/00 | (2006.01) | |
| H04N 9/04 | (2006.01) | |

(52) U.S. Cl.
CPC .............. *G01N 21/90* (2013.01); *G01N 21/27* (2013.01); *G01N 21/9036* (2013.01); *G01N 21/9054* (2013.01); *G01N 21/9072* (2013.01); *G06T 7/0008* (2013.01); *H04N 9/04* (2013.01)

(58) Field of Classification Search
CPC ................. G01N 2033/0081; G01N 21/909; G01N 21/9054
USPC ............ 348/127; 356/239.4, 240.1; 209/939; 382/142
See application file for complete search history.

(56) References Cited

U.S. PATENT DOCUMENTS

| | | | | |
|---|---|---|---|---|
| 4,731,649 A * | 3/1988 | Chang | ................ | G01N 21/9054 250/223 B |
| 5,072,108 A * | 12/1991 | Ishikawa | .................. | G01V 8/20 250/223 B |
| 6,175,107 B1 * | 1/2001 | Juvinall | ............. | G01N 21/9054 250/223 B |
| 6,239,869 B1 * | 5/2001 | Heuft | .................. | G01N 21/9018 356/239.5 |
| 7,911,602 B2 * | 3/2011 | Schlieper | ........... | G01N 21/4738 356/239.4 |

(Continued)

FOREIGN PATENT DOCUMENTS

DE    29907762    10/1999

*Primary Examiner* — Thai Tran
*Assistant Examiner* — Mishawn Hunter
(74) *Attorney, Agent, or Firm* — Occhiuti & Rohlicek LLP

(57) ABSTRACT

An inspection device for monitoring bottles includes a lighting unit, a color-sensitive camera, and a control-and-evaluation unit. The lighting unit is arranged above a transport path of bottles to be examined and has a light-source circuit-board having light sources that emit light having a light-source color. The control-and-evaluation unit changes the light-source color to a bottle color that is determined in a region of a mouth of a bottle.

22 Claims, 3 Drawing Sheets

(56) References Cited

U.S. PATENT DOCUMENTS

| | | | | |
|---|---|---|---|---|
| 8,284,305 B2* | 10/2012 | Newcomb | ............... | G06K 9/20 |
| | | | | 348/131 |
| 8,477,989 B2* | 7/2013 | Bresolin | ............ | G01N 21/9508 |
| | | | | 348/127 |
| 9,329,135 B2* | 5/2016 | Diehr | ................... | G01N 21/90 |
| 2006/0000968 A1* | 1/2006 | Katayama | .......... | G01N 21/9054 |
| | | | | 250/223 B |
| 2006/0045324 A1* | 3/2006 | Katayama | .......... | G01N 21/9054 |
| | | | | 382/142 |
| 2006/0126060 A1* | 6/2006 | Colle | ................ | G01N 21/9054 |
| | | | | 356/239.4 |
| 2008/0093537 A1* | 4/2008 | Novini | ................. | B07C 5/3408 |
| | | | | 250/223 B |
| 2011/0058156 A1* | 3/2011 | Niedermeier | ...... | G01N 21/9081 |
| | | | | 356/51 |
| 2011/0102783 A1* | 5/2011 | Wiemer | ............. | G01N 21/9018 |
| | | | | 356/239.4 |
| 2011/0140010 A1* | 6/2011 | Akkerman | ........ | G01N 21/9018 |
| | | | | 250/553 |

* cited by examiner

EMPTY BOTTLE INSPECTION

RELATED APPLICATION

This application is the national stage entry under 35 USC 371 of PCT/EP2012/001895, filed on May 2, 2012 which, under 35 USC 119, claims the benefit of the priority date of German application DE 10 2011 106 136.7 filed on Jun. 10, 2011, the contents of which are herein incorporated by reference.

FIELD OF DISCLOSURE

The invention relates to an inspection device, for monitoring bottles or similar containers, comprising at least one lighting unit and at least one camera, wherein the at least one lighting unit is arranged above the bottle to be examined. However, the invention also relates to a method for empty bottle inspection, especially of a mouth region of the bottle, with the inspection device.

BACKGROUND

Bottles or similar containers can be used for liquids, e.g. for beverages. The containers can be made of a transparent or translucent material, for example of glass, or of a translucent plastic, e.g. PET. Glass bottles, in particular, can have different colorings with, for example, brown and green but also blue bottle colors mentioned only as examples. The bottles, or similar containers are guided, when empty, preferably after they have been cleaned, on a transporter past the inspection device. It is known that bottles can also be closed with so-called crown caps or other oxidizable capping elements. In that regard, it is possible that the crown cap will have oxidized and thus that rust from the crown cap, or from another oxidizable capping element, will be deposited in the mouth region of the bottle. If the inspection device detects deposited rust, although the empty bottle has passed the cleaning device, the bottle concerned is rejected from the bottle flow, at a suitable location, and either destroyed or re-enters the bottle flow before the cleaning system.

Normally, the lighting unit emits a light of the same spectrum, thus in the same color, which is why the inspection device does not always achieve a reliable inspection result for bottles of different colors. Hence, it is possible for a bottle that has rust to be mistakenly classified as a good bottle, even though the bottle should have been separated out due to the existing contamination. If such a bottle enters the further production process, this can lead to unproductive downtime, as the filled product, from a hygienic perspective, will not be perfect due to the possible contact with the contamination. If such a bottle reaches the consumer, the maker of the product, or the system manufacturer, can furthermore suffer substantial damage.

SUMMARY

Thus, the task underlying the invention is to improve an inspection device, and also an inspection method of the type already mentioned, by simple means such that the above-mentioned disadvantages during an inspection of the containers or bottles are avoided, especially for bottles of different colors.

Proposed is an inspection device for monitoring bottles or similar containers, comprising at least one lighting unit and at least one camera, wherein the at least one lighting unit is arranged above the bottle to be examined. It is expedient that the lighting unit be designed as a light-source circuit-board, the light sources of which emit light that can be changed at least in color and/or in the respective intensity to a bottle color determined in the region of a bottle mouth, wherein the light sources are arranged in radially spaced rows, i.e. in light source rings, each concentric about a midpoint of the light source circuit board, and emitted light is coupled at least partially into the interior of the bottle mouth wall.

Expediently, the light sources are designed as LEDs, each of which emits light of a common light space. As an example, the LEDs can emit light of the RGB light space (Red-Green-Blue). This, of course, is not intended to be limiting.

It is also beneficial if the light-source circuit-board has a control-and-evaluation unit or is selected by means of a control and evaluation unit such that the individual concentric rows of light sources, hence the individual light source rings, are selectable. It is also expedient if, in addition, individual light sources of a respective concentric row that is in the respective light source ring are separately selectable. With this measure, a particular desired and always changeable light pattern, even of very different intensity, in particular color-modulated, can be generated on the light-source circuit-board. It is expedient if the lighting unit, that is the light source circuit board, is stroboscopically selected, hence flashes, preferably flashing in a color-modulated and/or intensity-modulated manner, if a bottle to be examined is in the inspection area.

As already mentioned, a part of the emitted light is coupled into the interior of the bottle mouth wall. Another part of the emitted light can be directed onto the outer circumference of the bottle mouth in order to slightly brighten it.

The mouth region of the bottle has a concave contraction, arranged on the outer circumference, underneath the mouth, at which rust preferably deposits. It is thus expedient if the emitted light is coupled into such a suitable location of the inner circumference of the bottle mouth such that the light again exits the area to be examined, so that, for example, the concave contraction can be reliably examined. In addition, the light radiated onto the outer circumference should also be directed so as to brighten the area to be examined, preferably the concave contraction.

If the light is coupled into the inner circumference of the bottle mouth region, that is from inside into the mouth wall, and again exits it at the outer circumference, an inspection with transmitted light is performed advantageously. Of course, the light is refracted in its beam path according to the laws of physics when entering the glass material but also when exiting the glass, which should be taken into account during the directed coupling-in, to be able to transilluminate the area to be examined with the required light. The light source circuit board will also emit directed light. In the process of brightening the mouth region, preferably the concave contraction, from outside, the incident light brightening is performed. The invention thus allows the combination of transmitted light and incident light, if required.

It is expedient if also the at least one camera is arranged above the bottle to be examined. Within the meaning of the invention, it is also advantageous if the camera is adapted to the color space of the light sources, for example, by having a color filter that is adapted to the color space of the light sources. For example, the at least one camera could thus also be an RGB camera.

To be able to examine the bottle mouth region for rust deposits with the camera arranged above the bottle, it is useful to provide at least a first, optical element that directs an image, or mirror image, of the bottle mouth region to the at least one camera. The optical element can be designed as a mirror and, in its respective design, is generally known in the technical field of empty bottle inspection. The camera can, of course, also be arranged laterally in relation to bottle and/or at bottle height and/or underneath the bottle.

It is also expedient if several first optical elements are provided in order to obtain an all-round image of the bottle mouth region. Therefore, preferably, four optical elements are provided, each of which images a certain bottle mouth portion towards the camera, wherein overlaps of adjacent images are always possible. The four partial images can be put together or evaluated in a control-and-evaluation unit.

The camera can preferably be arranged with its optical axis transverse and perpendicular to the vertical bottle axis so that the inspection device, in addition to the first optical elements, can still have second and third optical elements that mirror the mentioned images to the camera.

With the invention, rust deposits or fine rust spots also become detectable due to the highly sensitive capture or evaluation. For this, a light adapted to the bottle color, that is color-modulated light, is emitted by the light sources, wherein, in the control-and-evaluation unit, which as mentioned is connected with the camera, nominal data i.e. nominal colors, is compared with actual data i.e. with actual colors of the inspection area, or evaluated. The nominal data is stored in the control-and-evaluation unit. In addition, the modulatable light intensity in the inspection area can also be measured. However, it is also expedient if the light sources, which are arranged in concentric light source rings, are selected as rings, ring portions, and/or individually, wherein a color variability and a respective desired light intensity can also be controlled.

Beneficially, the invention also combines transmitted light, adapted in terms of color and/or also in its intensity, with the light space-camera capture. In particular, the light color of the light to be emitted is adapted to the bottle color or the glass color. For example, it has been found that light that is predominantly green/blue light is less suitable for brown bottles. As a result, the light to be emitted has its red proportion increased to improve the transmission. Thus, it is expedient to first detect the glass color in order to select, with the controller, the light source circuit board or the individual light sources such that the most beneficial inspection light (color-modulated, intensity-modulated, directed for correct internal coupling-in) is always emitted for the glass color of the bottle to be inspected.

Of course, the inventive idea with the adapting light can also be transferred to other inspection tasks. The use of the invention for rust detection is only cited as an example and is in no way intended to be limiting.

DESCRIPTION OF THE DRAWINGS

Further advantageous configurations of the invention are revealed in the subclaims and the following figure description, with FIG. 1 showing a basic structure of the inspection device, FIG. 2 showing an enlarged representation of a lighting unit, and FIG. 3 showing an inspection device according to the invention in side view.

DETAILED DESCRIPTION

Figure 1:
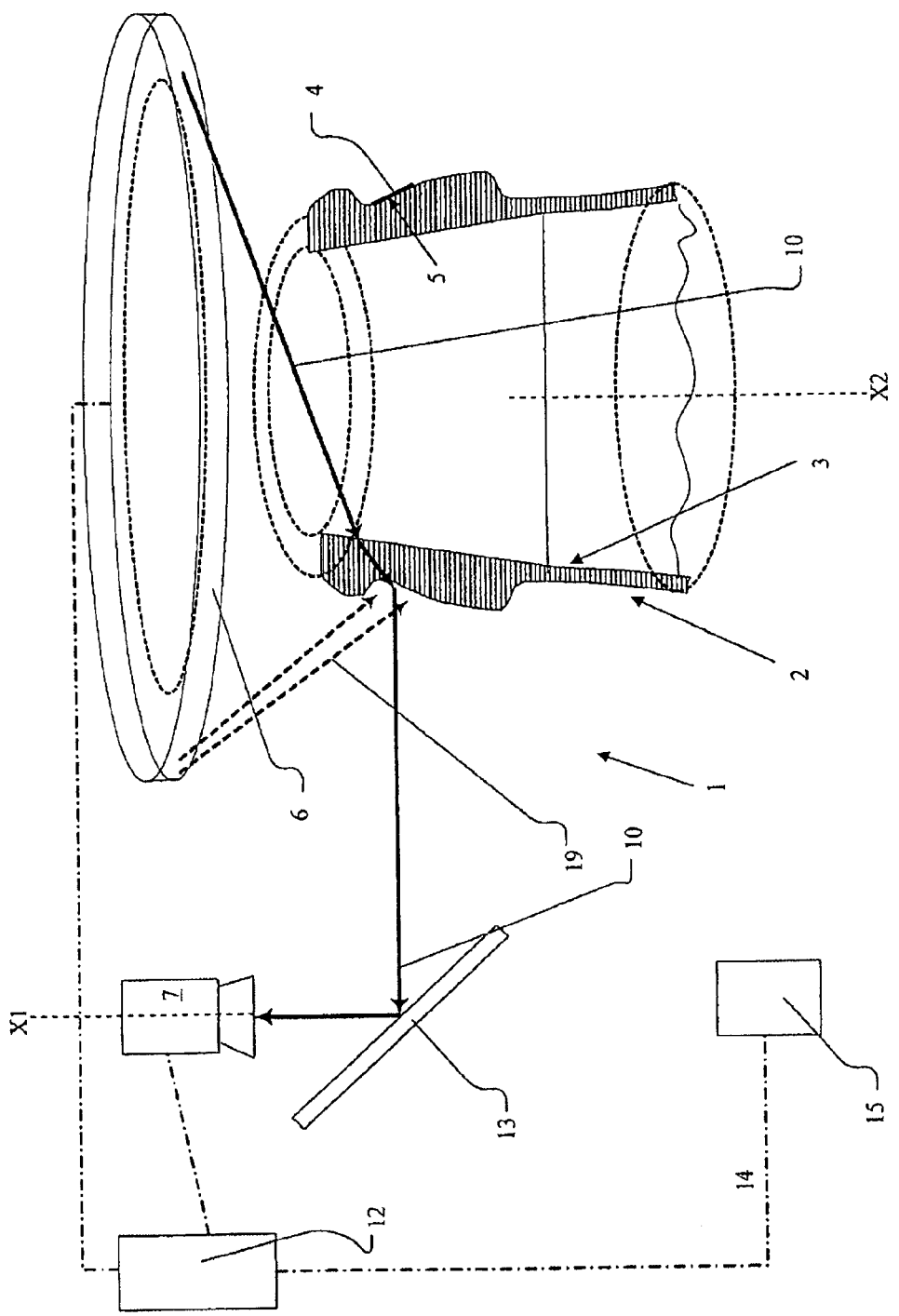
Figure 3:
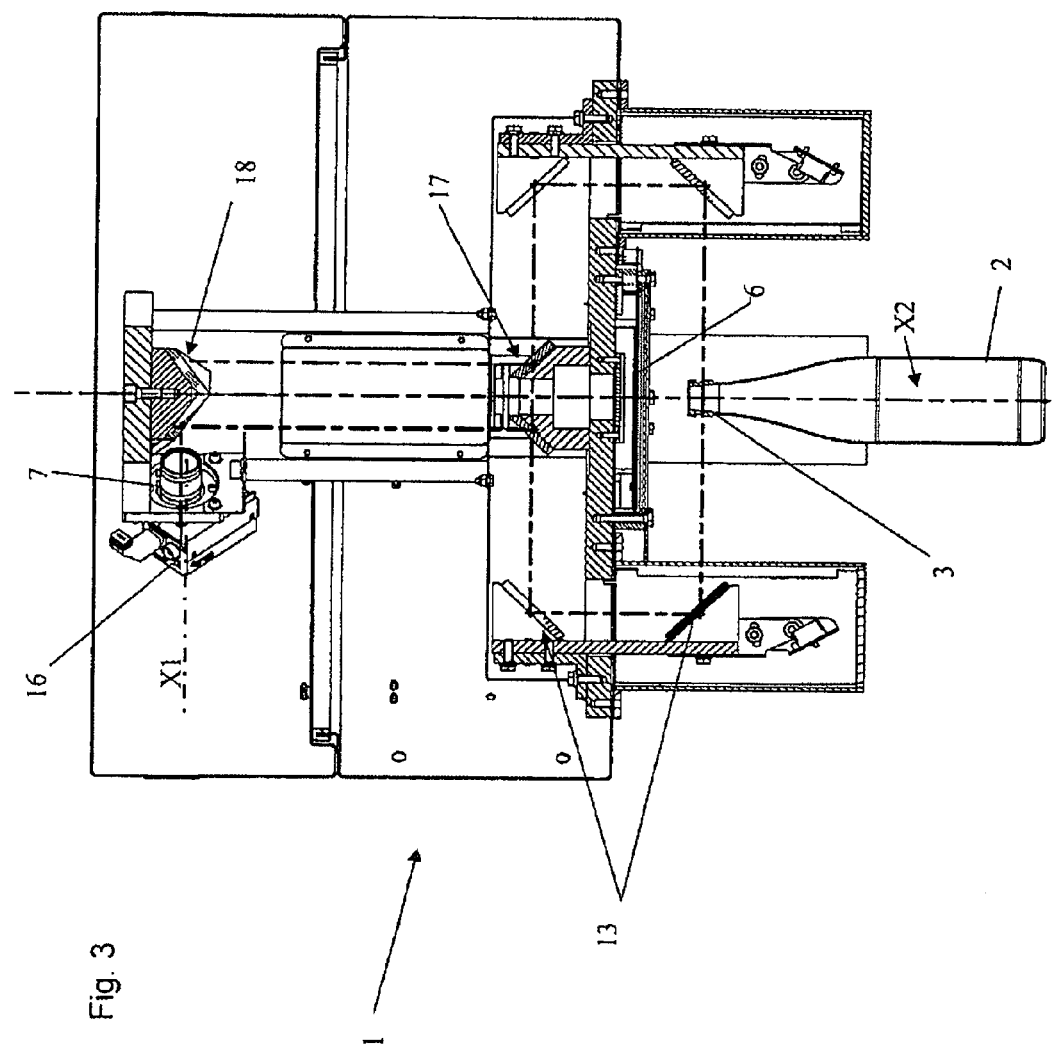

In the different figures, identical parts are always denoted by the same reference symbols, which is why these, usually, are only described once. In FIGS. 1 and 3, optical beam paths of the mirror images are dashed and not separately provided with reference symbols.

FIG. 1 shows an inspection device 1 for monitoring bottles 2 or similar containers. Hereinafter, bottles 2 or similar containers are generally designated as bottle 2. The bottle 2 can be made of a transparent or translucent material, preferably of glass, or of a translucent plastic, e.g. PET. The material or the glass of the bottle can be any color, with blue, green or brown being common examples.

The bottle 2 has a bottom and a side wall. A bottle mouth 3 is arranged opposite the bottom. With the inspection device 1, preferably, the bottle mouth 3 of the bottle 2 is to be examined, preferably after it has been cleaned, e.g. for contamination such as rust deposits 4.

The rust deposits 4 can stem from crown caps with which the bottle 2 had been closed. Such rust deposits 4 preferably collect on a concave contraction 5 at the bottle neck.

The inspection device 1 has at least one lighting unit 6 and at least one camera 7, wherein the at least one lighting unit 6 is arranged above the bottle 2 to be examined. The lighting unit 6 is designed as a light source circuit board 6 (FIG. 2), the light sources 8 of which emit light that can be changed in color and/or in the respective intensity. The color can be changed to a bottle color determined in the region of a bottle mouth 3. The light sources 8 are arranged in radially spaced light source rings 9, each concentric about a midpoint of the light source circuit board 6. Emitted light 10 is coupled at least partially into the interior of the bottle mouth wall.

Figure 2:
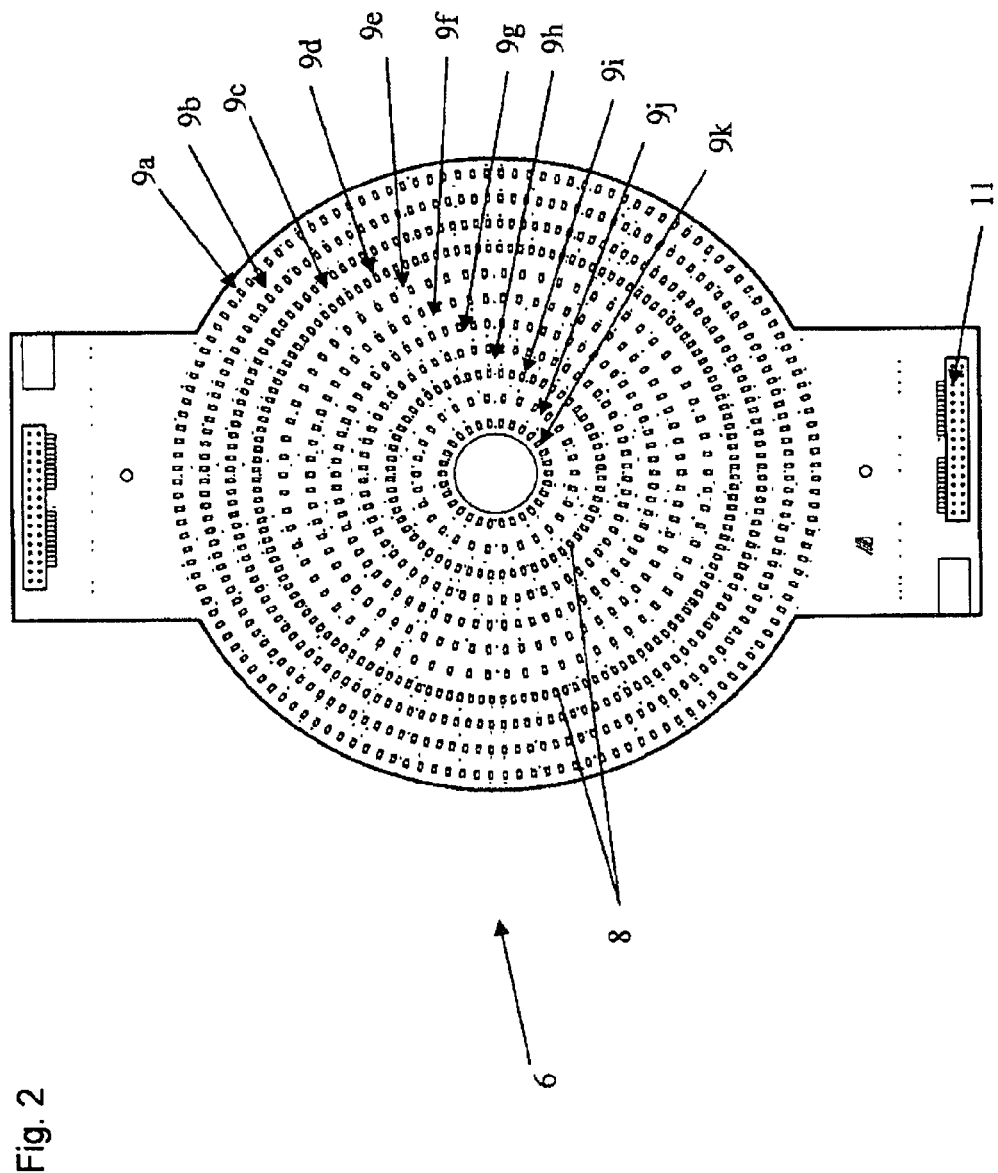

The lighting unit 6 or the light source circuit board 6 is shown more clearly in FIG. 2, in which the concentric light source rings 9 with respective light sources 8 can be seen. As an example only, eleven light source rings 9a to 9k (the designations are selected from outside to inside) are arranged on the light source circuit board 6. In the respective light source ring 9a to 9k, the adjacent light sources 8, seen in the circumferential direction, for example, are each equidistant. As can be seen, however, the light source distances of the respective light can be made to be different. For example, the light source rings 9a to 9d and 9k and 9i have a smaller light source distance than the light source rings 9e to 9h and 9j, which, of course, is only to be understood as an example and is in no way limiting. Any light source distances in the respective light source rings are conceivable. More or fewer than eleven light source rings 9 are also conceivable. Deviating from the ring-based arrangement of the light sources 8, any conceivable pattern with the light sources 8 can of course be arranged on the light source circuit board 6. For example, a cross pattern is conceivable.

The light source circuit board 6 has connections 11 for a control-and-evaluation unit 12. The light sources 8 are preferably designed as LEDs that can emit light of different colors and different intensities. The light sources 8 of the light source circuit board 6 can be selected by means of the control-and-evaluation unit 12. Advantageously, the light sources 8 of the individual light source rings 9 can be selected as rings, ring portions and/or individually. Beneficially, it is possible to select the light sources 8 such that light of adapted color and adapted intensity can be emitted from the lighting unit 6, wherein the light to be emitted, in particular, is adapted to the respective glass color. In particular, it is possible to differently control the intensity of the light to be emitted in different areas of the light source circuit board 6. A selection that causes light patterns to be emitted is of course possible.

As can be seen in FIG. 1, emitted light 10 is coupled into the inner circumference of the bottle mouth 3 or the inner glass wall, wherein the outer circumference of the area to be examined is irradiated with light 19 that is also emitted from the lighting unit 6. It is beneficial that here, as mentioned above, different light intensities can be controlled so that the outer circumference is only brightened by the light 19, wherein the light 10, which is directed and coupled in, can have a greater intensity. The transmitted light inspection and the incident light brightening can be performed with the invention and with a single lighting unit 6.

In FIG. 3, a first optical element 13 can also be seen. The first optical element 13 images a circumferential portion of the area to be examined so that the camera 7 can take a mirror image of the area to be examined. The camera 7 directs the mirror image as actual data to the control-and-evaluation unit 12. In the control-and-evaluation unit 12, or in its evaluation section, nominal data is stored. This nominal data can be compared with the actual data received by the camera 7. As the emitted light, in its color portions, is adapted to the bottle color, it is expediently envisaged that, in the control-and-evaluation unit 12, an adjustment of the actual colors with the nominal colors is performed. If deviations above defined limit values are detected, for example as a result of detection of rust deposits 4, a rejection signal 14 is directed to a rejection station 15, which then removes the bottle 2 concerned from the bottle flow.

To be able to achieve a circumferential image of the area to be examined, it is advantageously envisaged that several first optical elements 13, for example four first optical elements 13, be provided and that each one image another circumferential area, wherein overlaps of adjacent circumferential areas are not detrimental. The four partial images are put together in the control-and-evaluation unit 12 to form an overall image. An evaluation of the respective individual partial images is also conceivable. Also conceivable is a configuration in which the bottle 2 rotates, i.e. is examined while rotating, so that a circumferential arrangement of the first optical elements 13 is not needed, and only a single optical element 13 is sufficient.

The light sources 8 each emit light from the same color space. Thus, it is also useful to design the camera 7 such that it is adapted to this color space. For example, the light sources 8 can emit light from the RGB color space (Red-Green-Blue), in which case the camera 7 should be designed as an RGB camera. The allocation of a corresponding color filter 16 to the camera 7, said color filter being indicated in FIG. 3, is possible.

As can be seen in FIG. 1, the camera's optical axis X1 is arranged parallel to the vertical bottle axis X2, but laterally offset from it. The camera 7 can be arranged above the bottle mouth 3. In contrast to this the camera 7 in the execution example relating to FIG. 3 is arranged with its optical axis X1 transverse, preferably perpendicular to the vertical bottle axis X2 above the bottle 2 to be examined. In FIG. 3, the four first optical elements 13 can also be seen, each of which images another circumferential area of the area to be examined.

As the camera 7 with its optical axis X1 is arranged transverse to the vertical bottle axis X2, there needs to be a redirection of the images that are taken by the first optical elements 13. This is achieved by means of second and third optical elements 17 and 18.

An expedient aspect of the invention is that the lighting unit 6, i.e. the light source circuit board 6, emits light adapted to the respective bottle color, i.e. color-modulated light, so that a reliable inspection, such as for possible rust deposits 4, can be performed. Corona-type activation of the light source rings 9 is conceivable, e.g. to achieve directed light. The transmitted light inspection is useful, in which emitted color-modulated light is coupled into in the interior wall of the bottle mouth 3. The transmitted light inspection can be combined with the incident light brightening. The physical refractions of the incident and exiting light can be seen in FIG. 1. The directed, color-modulated light can be coupled in such that an exit at the area to be examined, i.e. preferably in the area of the concave contraction 5, is ensured.

The invention claimed is:

1. An apparatus comprising an inspection device for monitoring bottles, said inspection device comprising a lighting unit, a color-sensitive camera, and a control-and-evaluation unit, wherein said lighting unit is arranged above a transport path of bottles to be examined, wherein said lighting unit comprises a light-source circuit-board having light sources that emit light having a light-source color, wherein said control-and-evaluation unit is configured to change said light-source color to a bottle color that is determined in a region of a mouth of a bottle, and wherein said light sources are arranged in radially spaced light source rings, each of which is concentric about a midpoint of said light-source circuit-board, and wherein emitted light is coupled at least partially into an interior of a wall of said bottle mouth.

2. The apparatus of claim 1, wherein said control-and-evaluation unit is configured to cause selected light sources to flash.

3. The apparatus of claim 1, wherein adjacent light sources in a light source ring are spaced apart by an identical distance.

4. The apparatus of claim 1, wherein said lighting unit is configured to emit variable intensity light.

5. The apparatus of claim 1, wherein said light sources comprise LEDs from which color-modulated light is emitted in a directed manner.

6. The apparatus of claim 1, wherein said light sources comprise LEDs from which intensity-modulated light is emitted in a directed manner.

7. The apparatus of claim 1, wherein said camera is configured to be above said mouth.

8. The apparatus of claim 1, further comprising a first optical element, wherein said first optical element reflects an image of an area to be inspected toward said color-sensitive camera.

9. The apparatus of claim 1, further comprising a plurality of first optical elements disposed to reflect an all-around image to said color-sensitive camera.

10. A method for monitoring bottles, said method comprising modulating color of light emitted by a lighting unit to maximize light transmission through a colored bottle, directing said modulated light through an open mouth of said colored bottle and onto an interior surface of said colored bottle, and capturing a transmitted portion of said modulated light, said method further comprising arranging said light sources in a light-source ring, and selecting light sources such that light from said light sources is coupled in a directed manner into an inner circumference of a mouth of a bottle to be inspected.

11. The method of claim 10, further comprising modulating intensity of said light.

12. The method of claim 10, wherein modulating said color of said light is carried out once prior to inspection of said bottle.

13. The method of claim 10, further comprising causing said light source ring to flash stroboscopically.

14. The method of claim 10, further comprising causing each of said light sources to emit light of the same color space.

15. The method of claim 10, further comprising illuminating a concave contraction of said bottle to be examined with incident light that is emitted from said lighting unit.

16. The method of claim 10, further comprising causing selected light sources to flash stroboscopically.

17. The method of claim 10, wherein modulating color of light emitted by a lighting unit comprises detecting a bottle color of said colored bottle, and based on said bottle color, selecting a color to be emitted by said lighting unit.

18. The method of claim 17, further comprising using actual data, which has been obtained by transformation of said captured transmitted portion of said light, to infer existence of rust adhering to an outer surface of said bottle, wherein using said actual data to infer existence of rust comprises comparing an actual color of said transmitted portion of said light with a nominal color.

19. A method for monitoring bottles, said method comprising modulating color of light emitted by a lighting unit to maximize light transmission through a colored bottle, directing said modulated light through an open mouth of said colored bottle and onto an interior surface of said colored bottle, and capturing a transmitted portion of said modulated light, said method further comprising further comprising transforming said captured transmitted portion of said light into actual data, comparing said actual data with nominal data, determining that a deviation of said actual data from said nominal data exceeds a specified limit value, and generating a rejection signal.

20. The method of claim 19, further comprising modulating intensity of said light.

21. The method of claim 19, further comprising causing each of said light sources to emit light of the same color space.

22. The method of claim 19, further comprising illuminating a concave contraction of said bottle to be examined with incident light that is emitted from said lighting unit.

* * * * *